United States Patent
Eagan et al.

(10) Patent No.: US 7,875,458 B2
(45) Date of Patent: Jan. 25, 2011

(54) APPLICATION OF TEST FOR RESIDUAL WAX CONTAMINATION IN BASESTOCKS TO CORRELATE WITH THE LOW TEMPERATURE VISCOMETRIC PROPERTIES OF FULLY FORMULATED OILS

(75) Inventors: James Douglas Eagan, Dorset (GB); James William Gleeson, Sewell, NJ (US); Lisa I-Ching Yeh, Marlton, NJ (US); Charles Lambert Baker, Jr., Thornton, PA (US); Christine A. Zielinski, Glen Mills, PA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 1047 days.

(21) Appl. No.: 10/981,956

(22) Filed: Nov. 5, 2004

(65) Prior Publication Data

US 2005/0112767 A1    May 26, 2005

Related U.S. Application Data

(60) Provisional application No. 60/525,054, filed on Nov. 25, 2003.

(51) Int. Cl.
*G01N 31/00*    (2006.01)

(52) U.S. Cl. .................... 436/60; 436/55; 436/139; 356/70; 73/53.05

(58) Field of Classification Search .............. 436/55, 436/60, 139; 356/70; 73/53.05
See application file for complete search history.

(56) References Cited

U.S. PATENT DOCUMENTS

| | | | | |
|---|---|---|---|---|
| 3,187,557 | A * | 6/1965 | Holbourne | 374/19 |
| 4,519,717 | A | 5/1985 | Jones et al. | 374/17 |
| 5,007,733 | A | 4/1991 | Laurent et al. | 356/70 |
| 5,088,833 | A * | 2/1992 | Tsang et al. | 374/17 |
| 5,651,614 | A * | 7/1997 | Juneau | 374/17 |
| 5,699,270 | A * | 12/1997 | Ashe et al. | 700/272 |
| 6,295,485 | B1 * | 9/2001 | Gleeson et al. | 700/272 |
| 2003/0075478 | A1 | 4/2003 | Beasley et al. | 208/33 |

FOREIGN PATENT DOCUMENTS

| | | |
|---|---|---|
| EP | 0 328 334 | 8/1989 |
| EP | 0 667 517 A1 | 8/1995 |
| GB | 1 304 073 | 1/1973 |

* cited by examiner

*Primary Examiner*—Lyle A Alexander
*Assistant Examiner*—Dennis M White

(57) ABSTRACT

Rapid determination of low temperature residual wax contamination in basestock oil provides a basis for real time correlation of basestock quality with the low temperature viscometric properties of fully formulated oils made using said basestock oil.

14 Claims, 7 Drawing Sheets

APPLICATION OF TEST FOR RESIDUAL WAX CONTAMINATION IN BASESTOCKS TO CORRELATE WITH THE LOW TEMPERATURE VISCOMETRIC PROPERTIES OF FULLY FORMULATED OILS

This application claims the benefit of U.S. Ser. No. 60/525,054 filed Nov. 25, 2003.

FIELD OF THE INVENTION

The present invention relates to methods for predicting the low temperature viscometric properties of fully formulated lubricating oils based on analyses of the wax content of the basestock used in producing such oils.

RELATED ART

During the dewaxing processes used to manufacture lubricating oil basestocks, breakdowns or inefficiencies in the processes can result in the presence in the basestock of a quantity of wax beyond that which is acceptable as being within proper basestock manufacture. Such contamination wax or excessive wax content can occur as a result of leakage of wax through rips or tears in the wax filter cloth used in solvent dewaxing processes or through the overloading of the solvent dewaxing processes or by basestock channeling through the catalytic beds used in catalytic dewaxing processes or by an over-loading of the catalytic dewaxing process or because of poor catalyst activity or selectivity or because the crude oil or feedstock to the process is significantly different than expected, resulting in inadequate dewaxing conditions.

As compared against wax present in the oil when the dewaxing process is not faulty or inefficient which wax is herein identified as "acceptable", residual wax contamination can result in the failure of any formulated oil made from such basestock oil containing residual wax to function properly at low temperature, that is, to have unsatisfactory low temperature viscometric properties.

The presence of such residual wax contamination, however, may not be readily determinable or detectable by standard wax identification techniques such as pour point or cloud point determination. That is, a basestock containing sufficient residual wax to cause any formulated oil made using the basestock to have unsatisfactory low temperature viscometric properties may still appear to be on-specification when examined using standard pour point and/or cloud point determination techniques.

Residual wax contamination, if sufficiently high, can result in the growth of wax crystals in the basestock. Wax crystals can result in a highly non-Newtonian increase in low temperature viscometrics in fully formulated oils resulting in high viscosities and/or poor pumpability at low temperatures. Wax crystals could also result in the diminution or loss of filterability in finished, fully formulated oils made from the basestock. In oils in which low temperature viscometrics or filterability is critical, such as engine oils or hydraulic oils or transmission fluids, the increase in low temperature viscometrics or the reduction in or loss of filterability result in a failure of the oil to function properly. Another potential issue with residual wax contamination is that wax crystals can form haze in the oil on standing which is undesirable from the perspective of the customers.

Growth of residual wax contamination wax crystals is typically a slow process and such crystals may become visible to the human eye only after several days or weeks have passed. Consequently, fully formulated oils can be produced using such base oils containing unidentified residual wax contamination resulting in the entire batch of product failing to meet viscometric specifications.

Most wax crystal determination techniques rely on human eye evaluation or on a gross change in basestock viscometrics. Thus, cloud point, overnight cloud point, and wax haze appearance are examples of tests that depend on human eye visualization. Pour point methods are examples of techniques that depend on a gross change in basestock viscometrics, whether the original manual pour point method is used which depends on the inability of the base oil to pour from an inverted beaker or automated methods are used such as the ISL pour point, Phase Technology pour, or the Herzog rotational pour point method. All these methods are gross wax identification methods suited for estimating whether the wax content of the base oils is acceptable. They are not well or adequately suited for the identification, quantification or demonstration of residual wax contamination. Most of these tests are also subjective, which contribute to their unreliability and wide range in accuracy and precision.

The substitution of an electronic analyzer which measures the onset and degree of haze or wax crystal formation by a change in the transmittance of light or in the degree or intensity of reflected light removes the human element from wax crystal formation determination. Such equipment is now available for the determination of cloud point, freeze point, and pour point. The analyzer uses light scattering through a small sample cell (about 0.15 ml) and detects the presence of solid wax particles from which light is reflected. The reflected light is detected continuously by a light sensor. Alternatively, the fall-off in transmittance of light through the sample cell by interfering wax crystals is also a means for detecting the presence of wax. As already indicated, however, cloud point, overnight cloud point, and pour point are not sensitive enough to be used as a basis for predicting the final low temperature viscometric properties of a formulated lube oil with respect to residual wax contamination. On occasion a fully formulated lube oil has been found to fail key low temperature viscometric properties for the oil, e.g., the cold cranking simulator (CCS) viscosity or the mini-rotary viscometer (MRV), despite passing the specification established for the oil with respect to cloud point and/or pour point.

Correlation between residual wax contamination of base oils and low temperature viscometric properties of finished oils, in real time, would permit formulated oils to be prepared which meet final product low temperature viscometrics.

DESCRIPTION OF THE INVENTION

Figure 1:
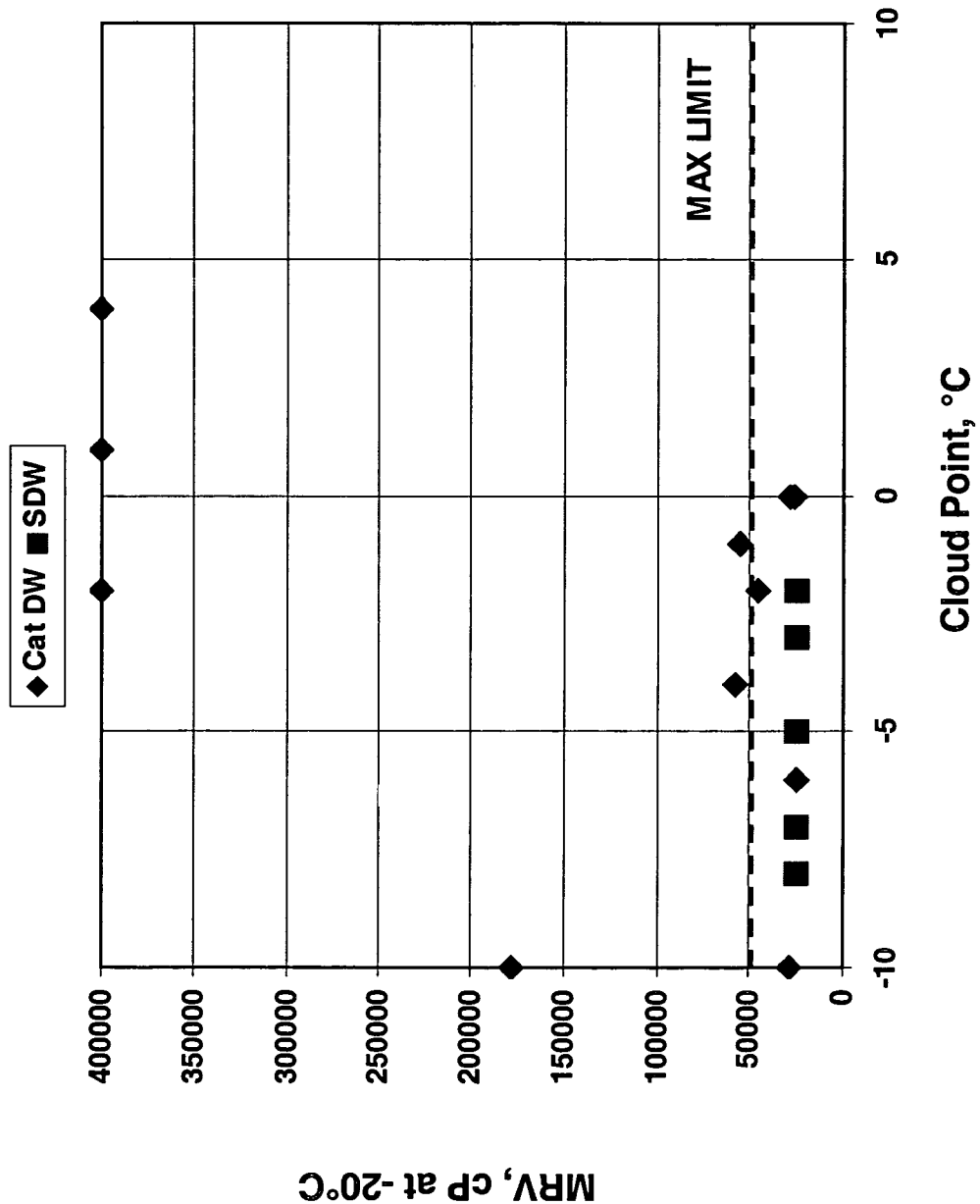
FIG. 1 presents the MRV results for 20W50 engine oil blends plotted as a function of the cloud points, determined by prior art technique, of the respective Bright Stock base oils used to make the blends.

The present invention is directed to a method for determining, in real time, the suitability of basestock oils for use as the basestocks in the production of fully formulated oils meeting product low temperature viscometric properties, which method comprises, in a first embodiment:

(a) selecting at least one low temperature viscometric property for the fully formulated oil;

(b) producing a training set by the steps of:
  (1) securing a sample of an appropriate candidate dewaxed basestock oil to be used in producing the fully formulated oil;
  (2) heating the basestock oil sample for a time and to a temperature sufficient to melt all the wax in the sample and, preferably, to also remove any water present in the sample;
  (3) agitating the heated sample to insure homogeneity;
  (4) cooling the oil in a sample cell equipped with heating and cooling means and instrumented for the measurement of reflection of light or transmittance of light generated by a source to a temperature in the range of between about 20° C. above the base oil specification pour point and 5° C. below the base oil specification pour point;
  (4a) waiting for the sample and test cell to stabilize, depending on the stability of the instrument after the temperature change and the size of the signal;
  (5) measuring the signal of scattered/reflected light off of or transmitted light through the sample at the temperature of step 4 after the stabilization period to secure a first intensity reading;
  (6) holding the sample at the temperature of step 4 for from 1 minute to 3 hours (preferably about 30 minutes to 90 minutes);
  (7) measuring the signal of scattered/reflected or transmitted light at the end of the hold time of step 6 to secure a second intensity reading and measuring any change in signal intensity (delta intensity of signal) between the first signal and the second signal reading;
  (8) formulating an oil product using the basestock and measuring the selected low temperature viscometric property or properties of step (a) associated with product quality;
  (9) repeating steps 1-8 using different temperatures between 20° C. above and 5° C. below the specification pour point as and if needed until a relationship is observed between the delta intensity of signal at the temperature of steps (4) and (6), and the selected formulated oil viscometric property or properties;
  (10) correlating the delta intensity of signal at the temperature of steps (4) and (6), to the selected low temperature viscometric property or properties;

(c) subjecting a base oil to steps 1-8;

(d) compare the delta intensity of signal of the base oil of step (c) with the correlation data base to predict whether a formulated oil possessing the selected low temperature viscometric property or properties can be made using said base oil.

Optionally and preferably, a step 9a can be practiced in which one or more additional samples of the same or different dewaxed base stock oils are subjected individually to steps 1-9 to create a data base of delta intensity of signal versus selected formulated oil low temperature viscometric property or properties for a multiplicity of base oil samples.

In a second embodiment, the present invention is a method for determining, in real time, the suitability of base stock oils for use as the base stocks in the production of fully formulated oil products meeting product low temperature viscometric properties, said method comprising:

(a) selecting at least one low temperature viscometric property for the fully formulated oil;

(b) producing a training set by the steps of:
  (1) securing a sample of an appropriate candidate dewaxed basestock oil to be used in producing the fully formulated oil;
  (2) heating the basestock for a time and to a temperature sufficient to melt all the wax in the sample and to remove any water present in the sample;
  (3) agitating the sample to insure homogeneity;
  (4) slowly cooling the sample in a sample cell equipped with heating and cooling means and fitted for the measurement of reflection of light or transmittance of light generated by a source from a temperature about 20° C. above to about 5° C. below, preferably about 10° C. above to about 2° C. below the pour point specification of the oil, measuring the reflection/scattering or transmittance signal, and measuring the ongoing change in signal intensity (delta intensity of signal);
  (5) formulating an oil produced using the basestock oil and measuring the selected low temperature viscometric property or properties of step (a) associated with product quality;
  (5a) optionally, repeating steps 1-5 for one or more additional samples of the same or different dewaxed base stock oils to generate a data base of delta intensity of signals versus the selected low temperature viscometric property or properties for a multiplicity of base oil samples;
  (6) correlating the delta intensity of signal to the selected low temperature viscometric property or properties;

(c) subjecting a base oil to steps 1-4;

(d) comparing the delta intensity of signal for the base oil of step (c) with the correlation data base to predict whether a formulated oil possessing the selected low temperature viscometric property or properties can be made using said base oil.

Optionally, the relationship between the delta intensity of signal and the selected low temperature viscometric property information generated for all unknown samples of step (c) can itself then be included into the data base as step (e).

In embodiment 1, steps 4 and 6, or embodiment 2, step 4, the temperature of the steps and the duration of step 6 in embodiment 1 or step 4 of embodiment 2 may be varied to obtain a suitable, robust correlation. This procedure can be accelerated by using the Temperature Ramp of embodiment 2 for a limited number of samples as in step 4, embodiment 2, to either select an appropriate target temperature for use in embodiment 1, step 4, or to select an appropriate Temperature Ramp, to generate the full database and correlation.

Low temperature viscometric properties of the fully formulated oils include but are not limited to mini-rotary viscometer (MRV) viscosity and yield stress, Brookfield viscosity, scanning Brookfield viscosity, cold cranking simulation (CCS), and pour point.

What constitutes a workable correlation between the selected low temperature viscometric property or properties and DI is left to the practitioner to determine for his particular base stock oil, finished formulated oil product and selected low temperature viscometric property or properties. In general, however, the selected low temperature viscometric property or properties is/are correlated to the temperature at which the intensity of the signal begins to increase, that is, the temperature at which the initial change in signal intensity begins, i.e., the onset temperature of the DI. This correlation is determined when a temperature ramp is employed. Alternatively and equally workable, the selected low temperature viscometric property or properties is/are correlated to the temperature at which a given delta intensity of signal is reached. Yet again, the selected low temperature viscometric property or properties is/are correlated to the delta intensity of signal measured at a given temperature. The given delta intensity of signal, the given temperature or the DI onset temperature is that which is determined from the generation of the training set and which aligns with the passing of the selected low temperature viscometric property or properties by the oil or oils once formulated into finished formulated product(s). Thus, the relationship between delta intensity of signal, the given temperature, or DI onset temperature and selected low temperature viscometric property or properties identifies the maximum DI value, of a base oil at a particular temperature, the temperature at a particular DI value, or the temperature at which DI onset occurs beyond which the formulated oil product made from the base oil fails to meet the preselected low temperature viscometric property or properties.

The correlation, therefore, relates DI or onset of DI with the passing or failing by the formulated oil products, made using the different oils, of the preselected low temperature viscometric property or properties. Each oil tested to generate the training set (and all subsequent base oils for commercial formulation purposes) will generate a particular DI, or exhibit the onset of DI in a temperature ramp, at a particular temperature.

In Embodiment 1 the practitioner reviews the selected low temperature viscometric property or properties for the particular formulated product for pass or fail and determines for the oil(s) that fails/fail the DI of the base oil(s) that failed compared against the DI of the base oil(s) that passed and the temperature at which this is observed. That temperature then becomes the given temperature at which the DI measurements are taken for all unknown base oils under consideration for use in the production of the particular formulated oil products.

In Embodiment 2 the practitioner similarly reviews the selected low temperature viscometric property or properties for the particular formulated product for pass or fail and determines for the oils that fail/fails the temperature in the temperature ramp at which the onset of the change in the signal intensity was observed (DI onset temperature) or a particular DI for the base oils that produced failing product.

That temperature then becomes the temperature in the temperature ramp at which the observation of the onset of a delta intensity or the achievement of a particular DI for an unknown oil under consideration for use in the production of the particular formulated product indicate the unsuitability of the base oil for the formulation.

In the practice of the present invention, the heating of the sample for a time and to a temperature sufficient to melt any wax in the sample and remove any water present in the sample, is typically a temperature of between about 50° C. to 150° C., preferably between about 60° C. to 120° C., more preferably about 100° C. for up to about 3 hours, preferably up to about 2 hours, more preferably about 10 seconds to up to 1 hour. The rate of heating to the desired temperature to melt the wax and drive off any water is not critical, but practically is between about 20° C./min. to 60° C./min., preferably about 4°° C./min. to 60° C./min., more preferably about 40° C./min.

The sample is then subjected to conditions sufficient to ensure the homogeneity of the sample. Such conditions can include vigorous shaking or stirring. If the sample is of sufficient size and the test cell is of sufficient size and durability this heating and agitation can be accomplished in the test cell. In a large enough cell, a magnetic stirrer can be used, but in general, shaking is sufficient. Alternatively, the sample can be heated and agitated in a separate vial or container, then transferred to the test cell.

Optionally, a step 3(a) can be practiced in either Embodiment 1 or Embodiment 2 in which the heated/agitated sample is then cooled at a consistent cooling rate to ambient condition. The heating and cooling to ambient conditions to melt any wax and remove any water can be repeated any number of times if deemed necessary or desirable by the practitioner for the given sample being evaluated and can either be done in the test cell or in a separate container with the oil cooled to ambient temperature being subsequently transferred to the test cell.

In the first embodiment wherein the sample is cooled to ambient temperature and then to a target temperature between about 20° C. above and 5° C. below the specification pour point of the oil, the rate of cooling in each step should also be kept consistent between samples, even when using different test instruments of the same type.

The rate of cooling to ambient conditions in embodiment 1 or 2 can be at any rate, provided it is consistent between samples. Preferred cooling rate to ambient conditions can range between about 5 to 100° C./min., preferably 30 to 50° C./min.

The rate of cooling to a temperature between about 20° C. above to about 5° C. below, preferably about 10° C. above to about 2° C. below the specification pour point in embodiment 1 can range between about 20° C./min. to 60° C./min., preferably about 40° C./min.

In Embodiment 1, once the sample is cooled to the chosen temperature between about 20° C. above to 5C below, preferably about 10° C. above to about 2° C. below the base oil specification pour point, the sample is subjected to a waiting period, if necessary, sufficient to permit the sample and test cell to stabilize, typically from zero to 500 seconds, preferably zero to 350 seconds, more preferably zero to 100 seconds.

In the second embodiment wherein the signal is read during the step of cooling the sample over the temperature range of about 20° C. above to about 5° C. below, preferably about 110° C. above to about 2° C. below the specification pour point of the base oil, this cooling is also at a consistent rate between samples and instruments and at about 0.1 to 1° C./min., preferably 0.2 to 0.75° C./min., more preferably about 0.25 to 0.50° C./min.

The oils used can be samples of actual oils employed in producing the desired product and made practicing solvent dewaxing or catalytic dewaxing. As used in the text and in the appended claims, the term "an appropriate candidate dewaxed basestock oil" means an oil or oils that at least meet the target pour point and/or cloud point for base oils typically employed to produce the type of formulated product for which the correlation is being generated. While this is preferred, it is not essential to the practice of the present invention. For example, if the typical base oil usually has a target pour point of no greater than −4° C., the oil or oils employed to produce the training set will similarly have pour point of about −4° C. That is, base oils having a pour point of 0° C., or +2° C., etc., would not be appropriate, but base oils having a pour point of, e.g., −2, −4, 8, −10° C., etc., would be appropriate. Alternatively, samples of actual oil known to be free of residual wax contamination and meeting the target pour point or cloud point for oils typically used to produce the desired formulated oil product can be spiked with various known quantities of wax of known properties. The spiked samples, if still meeting the target pour or cloud point, can then be used to produce the delta signals set and employed to make formulated oils to establish whether the viscometric property or properties of interest for such formulated oils are met and to create a data base correlating the delta signal with the selected low temperature viscometric property or properties.

The most reliable and robust correlation of residual wax contamination measurement to the selected low temperature viscometric property or properties will be obtained by representing the widest range of residual wax types and concentrations to be anticipated and predicted in the data base. This is because the type and concentration of residual wax can affect both the light scattering efficiency and the low temperature viscometric property. The reliability of the correlation can be reduced both by the omission from the data base of samples with the full range of residual wax types and concentration and by inclusion in the data base of samples with extraordinary residual wax types and/or concentrations that can bias or skew the correlations obtained.

In order to ensure the reproducibility and reliability of the data, it is important, as anyone skilled in the art will know, to be consistent with respect to those parameters, measurements and steps which are subject to variability, including the formulations of the final, finished product. With respect to the base oils themselves, the base oils are dewaxed by either solvent dewaxing or catalytic dewaxing processes. While not necessary as demonstrated in Example 1, it is desirable and preferred that the base oils which are evaluated or are to be evaluated for use as potential appropriate base stock(s) for the production of any given formulated product be dewaxed in the same manner, that is, catalytic dewaxed stock(s) should be compared and grouped with catalytic dewaxed stock(s), preferably produced using the same catalytic process while solvent dewaxed stock(s) should be compared and grouped with solvent dewaxed stock(s), preferably produced using the same solvent dewaxing process. The correlations generated in the present invention are specific for each different formulation considered.

Thus, the relationship between delta signal intensity and the selected formulated oil low temperature viscometric property holds true for formulated products made using the same combination of additives. Changes in additives, such as, e.g., viscosity index improvers or pour point depressants, result in the formulations being different, even if nominally producing the same final product test results. Such difference in additives can produce different results, oils giving passing results using one additive package now giving different results or producing failing results when using a different additive package.

The correlations produced for one oil or set of oils for a particular formulated oil product low temperature viscometric property or properties should not be used as a basis for predicting the passing or failing of that or those oil(s) for any particular low temperature viscometric property or properties, even if the same property or properties, for clearly different products; e.g., a correlation for oils(s) for, e.g., an engine oil product should not be used as a basis for prediction for, e.g., automatic transmission fluids.

Similarly, once a cooling profile is chosen, it is important to use the same cooling profile with respect to all base oil samples used to create the data base and all base oil unknowns evaluated for the production of a particular finished formulated oil product. The dimensions of the test cells, material of test cell fabrication, light source, measurement device, etc, must be kept as uniform and consistent as possible between samples to eliminate any variable other than the residual wax contamination of the base oil sample. Even the base oil heating temperature, time and method for agitation to insure homogeneity and cooling to ambient conditions should be kept the same between samples to remove any possible source of unanticipated variance.

Various instruments exist or can be readily fabricated to practice the present invention. Suitable instruments for making light scattering measurements include the PV70 Analyzer from Phase Technologies (Richmond, British Columbia, Canada) and the Hach 2100AN Turbidimeter (Hach Inc., Colorado). Other instruments suitable for making light transmission measurements are any of the UV-Vis, Near IR spectrophotometers (e.g., Perkin Elmer, Norwalk, Conn.).

Broad or narrow banded light within the UV, visible and/or IR wavelength region of the spectrum can be used as the light source, provided once a light source and wavelength are selected the selection is held constant for all base oils evaluated to create the data base and for all unknown oil samples tested for any particular finished formulated oil product.

Only such uniformity will permit the information contained in the data base to be used with confidence when evaluating unknown base oils for use in producing particular formulated oil products.

Near IR, such as that with a wave length between about 700 and about 1000 nm, preferably about 820 nm to about 900 nm, is useful for application to the widest variety of samples to avoid interference by absorption instead of scattering by some samples, especially those of a dark color.

To ensure that measurements made with an instrument at one time can be compared to those made at another time and that measurements made on one instrument can be compared to those made on another instrument, the instrument must be calibrated. Light scattering instruments can be calibrated by measuring the signal intensities for standards of known turbidity. Suppliers of such standards include Hach and GFS Chemicals. The instrument signal is correlated to the known values, usually with a linear function. The correlating function is applied to the signal intensity measured on a test sample.

For some instruments, the dependence of the signal on particle size may vary over time or from instrument to instrument. If so, this effect should also be calibrated. This can be done over the particle size range of interest (typically about 0.1 to 10 microns) by measuring the signal intensity from suspensions of beads of known, preferably uniform, particle size. The instrument is adjusted until the variation in signal with particle size is consistent over time or from instrument to instrument.

Calibration of the instrument to ensure consistent reading from the same instrument and reliable read-across capability between different instruments of the same type is a technique well known to and appreciated as important by practitioners of chemical analysis and analytic technology in general.

It is this determination of residual wax content as evidenced by a delta intensity of signal at low temperature in a short period of time which permits the formulator to make a real time determination of the suitability of any base oil batch for use in formulating finished product before using the base oil to actually produce the formulated finished product, with confidence that the formulated oil will meet low temperature viscometric property targets. It also enables a refiner to adjust dewaxing and other operations to make basestock that will be suitable for use in formulating finished products. It permits refiners to make adjustments on the fly so that the basestock produced will make formulated finished products meeting low temperature viscometric property specifications.

EXAMPLE 1

One of the basestock grades which is produced at most refineries is Bright Stock. This grade is produced either using a catalytic process (Cat DW) or a solvent dewaxing (SDW) process which uses solvents such as liquid propane or a mixture of methyl ethyl ketone (MEK) and toluene as the dewaxing solvent.

Depending on the processing conditions used and the mechanical state of the processing equipment, contamination by residual wax can occur. As noted earlier, the wax contamination may occur through rips or tears in the dewaxing filter cloth used in the SDW process, or by bypassing, channeling or poor catalyst selectivity in the Cat DW process.

Several samples of Bright Stock from various refinery sources and produced using the SDW or Cat DW process were evaluated in a study to determine the extent to which residual wax contamination was present, and to quantify the differences among the samples with respect to the mini-rotary viscometer (MRV) low temperature viscometric property of an engine oil formulated using the samples. As an example of the prior art used to detect residual wax contamination, the cloud point (ASTM D2500) was determined for each of the Bright Stock samples.

As a demonstration of the present invention, a Phase Technology analyzer using visible red light scattering was used to analyze the same samples. The samples were heated in an oven at 100° C. for about 1 hour, allowed to cool on a bench-top for 30 minutes, then inserted in a test cell and analyzed in the analyzer. A 0.15 ml portion of the sample is pipetted into the instrument's shallow cylindrical sample cup, which is about 1 cm diameter and has a mirrored surface at the bottom. The top of the cup is open to the sample compartment and faces the optical detector in the cover of the compartment. Light from the red LED source is directed at an oblique angle toward the center of the mirrored bottom of the sample cup. If no particles are present in the sample, the light reflects off of the mirror and away from the detector. If particles are present, they scatter some of the light toward the detector, where it is registered as an increase in signal intensity. The temperature of the cup is controlled by a Peltier device. The sealed sample compartment is purged with dry gas during the temperature program. The following temperature profiles were employed during the analyses.

| Step | Start Temperature, ° C. | End Temperature, ° C. | Rate, ° C./Minute | Soak, Seconds |
|---|---|---|---|---|
| Profile B | | | | |
| A | ambient | 60 | 40 | 10 |
| B | 60 | 20 | 40 | 0 |
| C | 20 | 60 | 40 | 10 |
| D | 60 | 0 | 40 | 1800 |

Time of Initial Intensity Measurement from start of step A (Sec.): 350 (about 60 sec after 0° C. is reached in step D)

| Profile D | | | | |
|---|---|---|---|---|
| A | ambient | 60 | 40 | 10 |
| B | 60 | 20 | 40 | 0 |
| C | 20 | 60 | 40 | 10 |
| D | 60 | 8 | 40 | 1800 |

Time of Initial Intensity Measurement from start of step A (Sec.): 350 (about 72 sec after 8° C. is reached in step D).

Each sample was first heated to 60° C. and held at that temperature for 10 seconds, then cooled to 20° C. Immediately following this, the sample was again heated to 60° C. and held there for 10 seconds. The purpose of the initial heating steps was to destroy the effects of thermal history of the sample which could affect the wax crystallization rate and the results of the analysis. Following the heating steps the sample was cooled to either 0° C. or 8° C. (see Profiles B and D, respectively, Step (D)). Following a stabilization period of 60-72 seconds after each sample reached the target temperature (0° C. or 8° C.), an initial measurement of the intensity of light scattered from the sample was recorded by the analyzer. The final intensity of scattered light at the end of the 30-minute soak period was also recorded. The difference between the initial and final intensity values was recorded as the delta intensity (DI) parameter, the primary result of the analysis using the Phase Technology analyzer.

The appropriate temperature profile selected for the analysis depends on the type of sample and the process used to produce it. The final soak temperature must be low enough to promote the growth of crystals of the contaminating residual wax component to an extent which can be reliably detected by the analyzer within a reasonable soak time (e.g., 30 minutes), but not so low that the growth of crystals from the acceptable wax normally present (i.e., not the contaminating wax component) would be promoted and add to/interfere with the DI value determined for the sample. Profile B (0° C./30 minutes) was found suitable for the particular Bright Stock samples produced by the SDW process, and Profile D (8° C./30 minutes) was found to be suitable for Bright Stock samples produced by the Cat DW process in this example. Both profiles were used to analyze the various samples of Bright Stock included in this study; other profiles would be suitable for other basestocks according to their viscosity grade and the dewaxing process used to produce them.

The same various samples of Bright Stock were used to prepare individual blends of 20W50 engine oil using fixed standard percentages of the respective components. In preparing this series of blends, only the Bright Stock component (source) was varied; each volume of oil came from the same physical sample as tested for residual wax content and a fixed percentage of each of the other components was used in preparing each of the blends. The properties of the engine oil blends and the DI/cloud point determinations of the respective Bright Stock samples used in the blends are summarized in Table 1. The mini-rotary viscometer (MRV) results of the 20W50 blends are plotted as a function of the cloud points of the respective Bright Stock components in FIG. 1. This graph illustrates the prior art technique used to detect wax contamination in basestocks. These results indicate that cloud point of the Bright Stock component is an unreliable indicator of the MRV of the corresponding engine oil. It is apparent that unacceptably high (failing) MRV results can occur over the full range of cloud points observed in this study, and that a definite cloud point above which failing MRV results would occur cannot be established with certainty.

Figure 2:
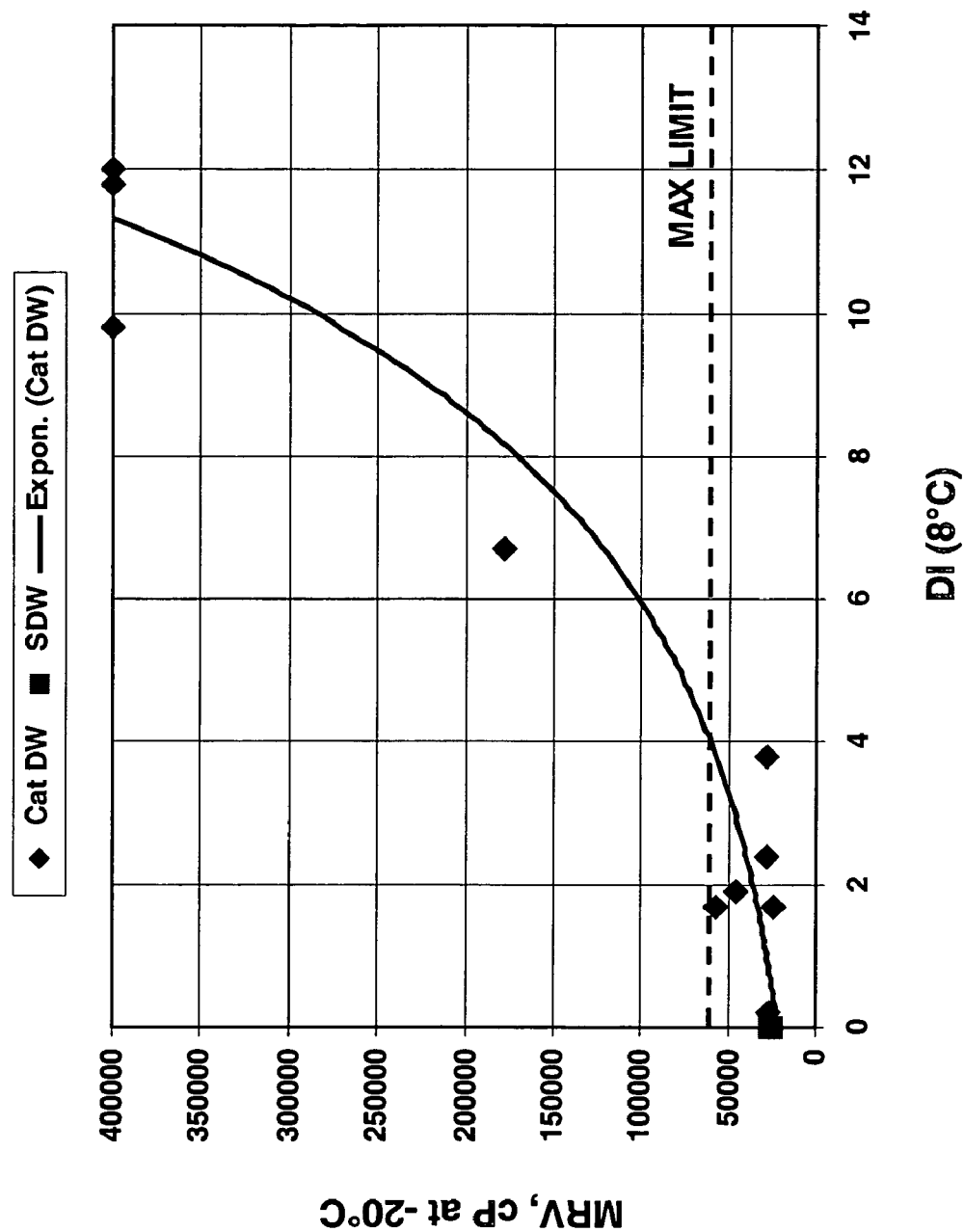
FIG. 2 presents the MRV results for 20W50 engine oil blends plotted as a function of the delta intensity (DI) values, determined according to an embodiment of the present invention, for the respective Bright Stock base oils used to make the blends.

The MRV results of the 20W50 blends are plotted as a function of the delta intensity (DI) values determined for the respective Bright Stock components in FIG. 2. Here, the DI values show a much improved correlation to the MRV results than do the cloud point results in FIG. 1. Based on the results in FIG. 2, it appears that a maximum DI value of about 4.0 for the basestock would be required to ensure that the MRV of the corresponding engine oil would not exceed the maximum limit. The results in FIG. 2 compared with those in FIG. 1 illustrate the improvement achievable with the present invention over the prior art.

TABLE 1

EFFECT OF BRIGHT STOCK QUALITY ON LOW-TEMPERATURE VISCOSITY 20W-50 BASED ON VARIOUS SAMPLES OF BRIGHT STOCK

| | | | | Sample | | | | | | |
|---|---|---|---|---|---|---|---|---|---|---|
| | | | | A | C | D | E | F | G | H | I |
| Dewaxing Process (1) | | | | Cat DW | PDU | Cat DW | Cat DW | Cat DW | Cat DW | Cat DW | Cat DW |
| Bright Stock wt % | | | | 37.96 | 37.96 | 37.96 | 37.96 | 37.96 | 37.96 | 37.96 | 37.96 |
| Light Neutral Basestock wt % | | | | 46.14 | 46.14 | 46.14 | 46.14 | 46.14 | 46.14 | 46.14 | 46.14 |
| Performance Additive wt % | | | | 15.9 | 15.9 | 15.9 | 15.9 | 15.9 | 15.9 | 15.9 | 15.9 |
| Test Results | Min | Max | | | | | | | | | |
| KV 40° C., cSt | | | D445 | 177.6 | 177.4 | 180.6 | 176.4 | 177.8 | 179.6 | 179.1 | 176.3 |
| KV 100° C., cSt | 18.0 | 20.0 | D445 | 19.34 | 19.04 | 19.32 | 19.06 | 19.21 | 19.14 | 19.12 | 18.92 |
| Pour, ° C. | | −15° C. | D97 | −17 | −20 | −18 | −20 | −19 | −21 | −17 | −17 |
| CCS −15° C., cP | | 9500 | D5293 | 9000 | 8530 | 9070 | 9020 | 8800 | 8450 | 8510 | 8850 |
| MRV −20° C., cP | | 60,000 | D4684 | 27900 | 25013 | >400000 | 45117 | >400000 | 57368 | 24100 | >400000 |
| MRV Yield Str −20° C., Pa | | <35 | D4684 | <35 | <35 | <350 | <35 | <280 | <70 | <35 | <280 |
| Delta Intensity (DI) Bright Stock Component | | | | | | | | | | | |
| 0° C., 30 minutes | | | | 21.5 | 0 | 60.6 | 18.2 | 70.9 | 9.9 | 10.5 | 85.7 |
| 8° C., 30 minutes | | | | 3.8 | 0 | 12 | 1.9 | 11.8 | 1.7 | 1.7 | 9.8 |
| Cloud Point of Bright Stock Component | | | D2500 | 0 | −3 | 1 | −2 | −2 | −4 | −6 | 4 |

| | | | | Sample | | | | | | |
|---|---|---|---|---|---|---|---|---|---|---|
| | | | | J | L | M | N | O | P | Q |
| Dewaxing Process (1) | | | | Cat DW | Cat DW | Cat DW | PDU | MEK/Tol | PDU | MEK/Tol |
| Bright Stock | | | | 37.96 | 37.96 | 37.96 | 37.96 | 37.96 | 37.96 | 37.96 |
| Light Neutral Basestock | | | | 46.14 | 46.14 | 46.14 | 46.14 | 46.14 | 46.14 | 46.14 |
| Performance Additive | | | | 15.9 | 15.9 | 15.9 | 15.9 | 15.9 | 15.9 | 15.9 |
| Test Results | Min | Max | | | | | | | | |
| KV 40° C., cSt | | | D445 | 172.2 | 173.1 | 175 | 174.6 | 178.1 | 176.1 | 174.6 |
| KV 100° C., Cst | 18.0 | 20.0 | D445 | 18.64 | 18.73 | 18.89 | 19.15 | 19.19 | 18.93 | 19.09 |
| Pour, ° C. | | −15 | D97 | −17 | −20 | −15 | −17 | −18 | −28 | −21 |
| CCS −15° C., cP | | 9500 | D5293 | 8390 | 8760 | 8830 | 7830 | 8820 | 8390 | 8430 |
| MRV −20° C., cP | | 60,000 | D4684 | 26100 | 27800 | 177810 | 24815 | 24900 | 24805 | 24910 |
| MRV Yield Str −20° C., Pa | | <35 | D4684 | <35 | <35 | <140 | <35 | <35 | <35 | <35 |
| Wax Haze Delta Intensity (DI) Bright Stock Component | | | | | | | | | | |
| 0° C., 30 minutes | | | | 30.6 | 58.1 | 84.4 | 0.2 | 0.1 | 0.6 | 0.4 |
| 8° C., 30 minutes | | | | 0.2 | 2.4 | 6.7 | 0.4 | 0.0 | 0.9 | 0.0 |
| Cloud Point of Bright Stock Component | | | D2500 | 0 | −10 | −10 | −7 | −2 | −5 | −8 |

(1) Key to dewaxing processes: Cat DW: Catalytic Dewaxing; PDU: Propane Dewaxing Unit; MEK/Tol: MEK/Toluene solvent Dewaxing.

EXAMPLE 2

Control of MRV in 20W-50 Engine Oil using 2500 SUS Base Stock Using Temperature Ramp The samples of Example 1 were also tested using the same equipment as in Example 1 but a temperature ramp as in Embodiment 2 rather than a constant temperature soaking period. The specification target pour point for these base stocks is −6° C. After holding the sample at 100° C. for 1 hour, then shaking vigorously the sample was put in the test cell and subjected to this temperature program:

| Step | Start temperature, ° C. | End temp., ° C. | Rate, ° C./minute | Time held at end temperature, second |
|---|---|---|---|---|
| A | ambient | 20 | 40 | 1800 |
| B | 20 | 60 | 40 | 10 |
| C | 60 | 20 | 40 | 0 |
| D | 20 | 60 | 40 | 10 |
| E | 60 | 14 | 40 | 10 |
| F | 14 | −2 | 0.25 | |

The start temperature in step A refers to the temperature of the test cell. The sample temperature is near 100° C. just before being put into the test cell.

The temperature cycling sequence of steps B and C is not a mandatory step but is helpful to further reduce water content and dissolve wax in samples that turn hazy quickly. A separate stabilization period after step E was not used in this case because the temperature ramp was started well above the temperature at which crystallization occurred.

Figure 3:
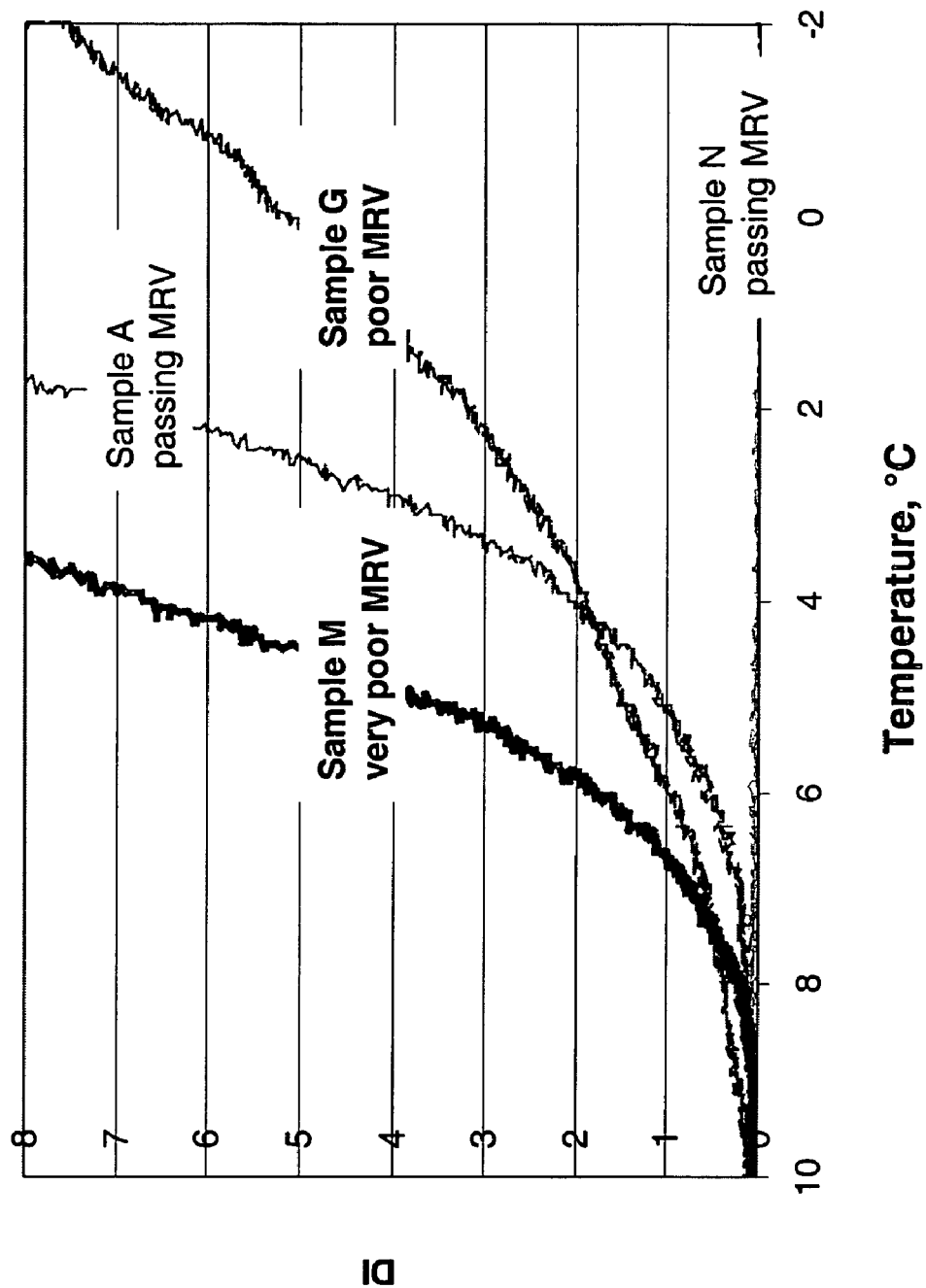
FIG. 3 presents a plot of the delta intensity versus temperature during a portion of a temperature ramp from 14° C. down to −2° C., for 4 bright stock base oil samples showing the good correlation of delta intensity measured at about +9 to +5° to low temperature MRV of 20W50 engine oils blended with these base oils.
Figure 4:
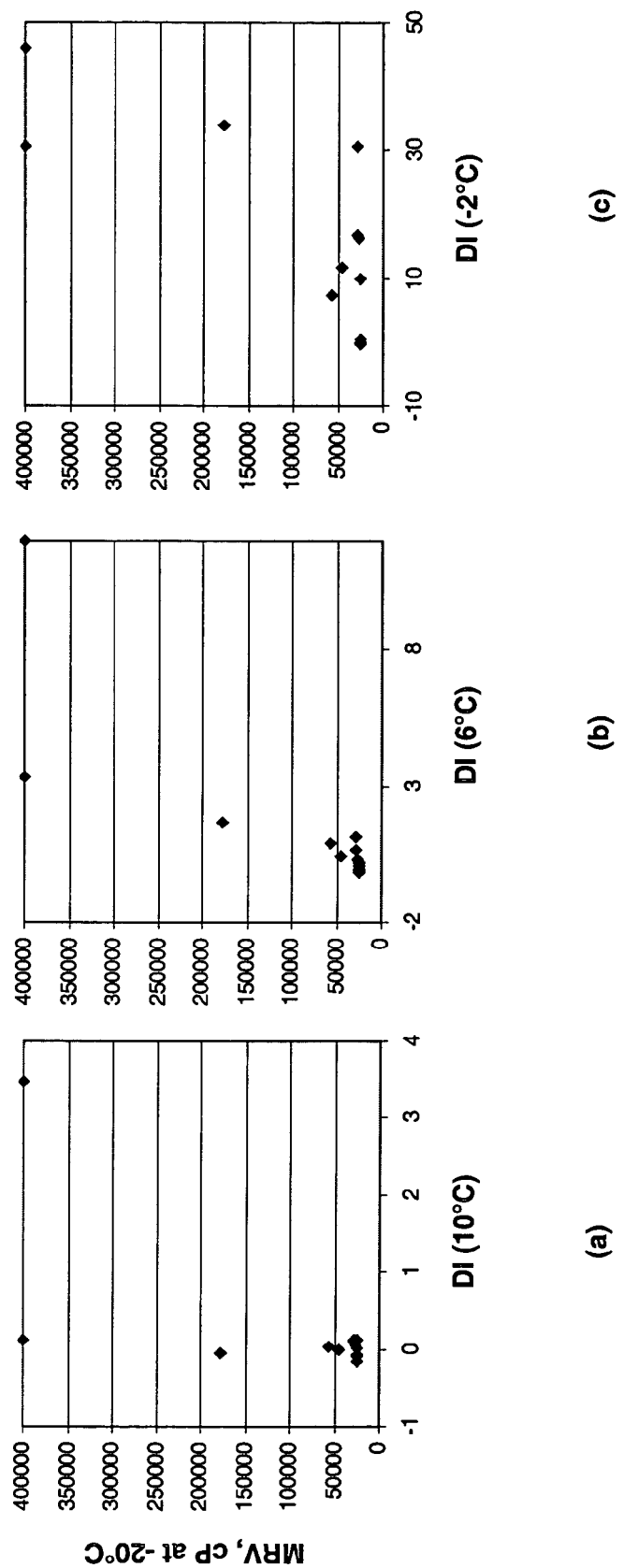
FIG. 4a, b and c plot the MRV versus DI data at 10° C., 6° C. and −2° C., respectively, for the 13 Bright Stock base oil samples used to make 20W50 engine oil blends showing that the DI data taken at 6° C. correlates best with the low temperature MRV viscometric property of interest.

In this experiment, in which the temperature was ramped from 14° C. to −2° C., Embodiment 2, various parameters are available to correlate to the MRV, including an onset threshold, i.e., temperature to reach a small constant signal increase, temperature to reach a larger delta signal, combinations of these and variations on these. Thus, the selected low temperature viscometric property or properties can be correlated to any combination of temperatures at which given delta intensities of signal are reached and delta intensities at given temperatures. For this purpose well known statistical techniques can be used such as multiple linear regression, principle component regression, and partial least squares analysis. See, e.g., "Multivariate Calibration", Harald Martens and Tormod Naes, John Wiley and Sons, 1989. The signal from four of the samples during this temperature ramp are shown in FIG. 3.

The difference between the signals at 10° C., 6° C. and −2° C. versus the signal at 14° C. at the start of the ramp are shown in the table. Of these temperatures, the signal at 6° C. gives the best correlation to the MRV. Low MRV viscosities and yield stresses are desirable in the formulated oil. The full database could then be developed using either this temperature ramp, a shortened temperature ramp (e.g., 14° C. to 6° C.), or a constant temperature near or at 6° C. with a soak (as in Embodiment 1). The delta signals using a constant temperature version at 8° C. described in Example 1 correlates well to MRV. The optimum light scattering or transmission parameter or combination of parameters may be selected using standard statistical techniques.

That the optimum temperature to use is so far above the target pour point in this example (+6° C. vs. −6° C. pour point) is surprising. The temperature ramp is useful in quickly identifying the appropriate temperature or temperature range to use to develop the correlation.

| | Sample Number | | | | | |
|---|---|---|---|---|---|---|
| | O | G | H | F | E | A |
| MRV @−20° C. yield stress, Pa, <35 | <35 | <70 | <35 | <280 | <35 | <35 |
| MRV @−20° C., visc, cP, 55600 | 24900 | 57368 | 24100 | >400000 | 45117 | 27900 |
| DI @ 10° C. | 0.1 | 0.0 | −0.1 | 0.1 | 0.0 | 0.1 |
| DI @ 6° C. | 0.2 | 0.9 | 0.0 | 3.3 | 0.4 | 0.7 |
| DI @ −2° C. | 0.4 | 7.4 | 9.9 | 30.6 | 11.6 | 30.6 |

| | Sample No. | | | | | | |
|---|---|---|---|---|---|---|---|
| | Q | P | N | M | J | L | I |
| MRV @−20° C. yield stress, Pa | <35 | <35 | <35 | <140 | <35 | <35 | <280 |
| MRV @−20° C., visc, cP | 24910 | 24805 | 24815 | 177810 | 26100 | 27800 | >400000 |
| DI @ 10° C. | −0.1 | 0.0 | −0.1 | 0.0 | 0.1 | 0.1 | 3.5 |
| DI @ 6° C. | −0.1 | 0.0 | −0.1 | 1.7 | 0.3 | 1.1 | 12.0 |
| DI @ −2° C. | −0.1 | 0.1 | −0.2 | 34.0 | 16.3 | 16.8 | 45.8 |

EXAMPLE 3

Control of MRV in 20W-50 Engine Oil Using Primarily 600 SUS Base Stock

It is required for product certification that the MRV viscosity and yield stress of engine oils be less than specified values. One such formulation contains 67 wt % of a 600 SUS (nominally 600 Saybolt Universal Seconds at 100° F.) conventional base stock. The target pour point for these base stocks is −6° C. Formulated oils were blended with the same performance additive components, except that different 600 SUS samples were used. Those samples had the same pour point. However, formulated oil MRV yield stress and viscosity differed. The samples were tested using the same equipment as was used in Examples 1 and 2. The oils were heated and held at 100° C. for about one 15 hour, heating being carried out with the sample in a vial in an oven. Following heating and agitation, the samples were placed in test cells. The table below shows the good correlation of DI to MRV when a constant temperature of −4° C. is used in the final 3600 second soaking step E of the following temperature program in Embodiment 1 after employing a stabilization time of about 74 seconds after the sample reached −4° C. Using a temperature of 0° C. and a time of 1800 sec during the final soaking step, along with a stabilization time of 60 sec, does not discriminate performance in this case.

| Step | Start temperature, ° C. | End temperature, ° C. | Rate, ° C./minute | Time at end temperature, second |
|---|---|---|---|---|
| A | ambient | 20 | 40 | 1800 |
| B | 20 | 60 | 40 | 10 |
| C | 60 | 20 | 40 | 0 |
| D | 20 | 60 | 40 | 10 |
| E | 60 | 2 | 40 | 10 |
| F | 2 | −8 | 0.25 | |

Figure 5:
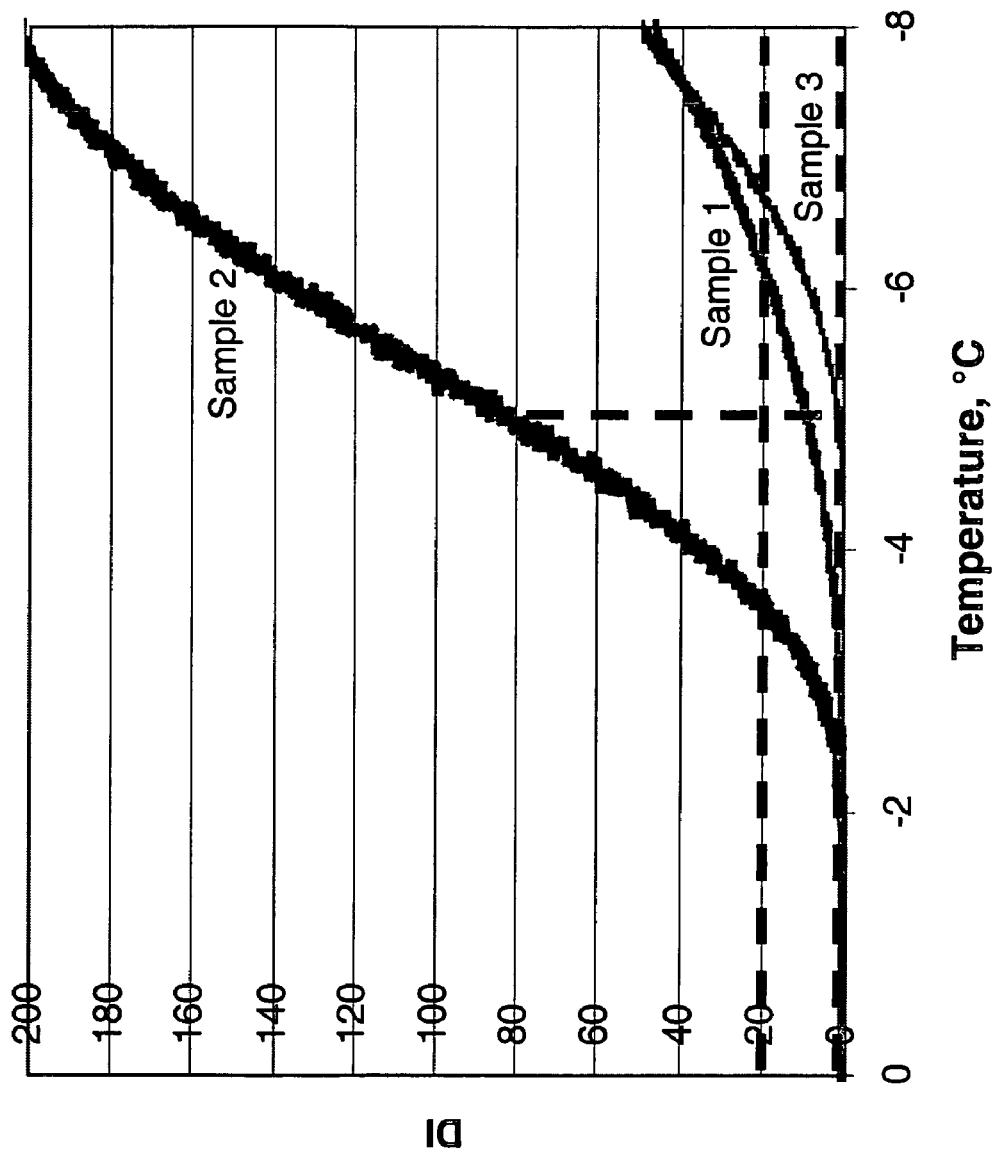
FIG. 5 presents a plot of DI versus temperature for three 600 SUS base oils tested to formulate a 20W50 Engine oil (Formulation 1) showing the DI for each sample as the temperature was ramped down from zero to −8° C.

Various parameters are available to control the MRV, including an onset threshold, temperature to reach a given signal increase, and signal increase at a given temperature. The onset threshold used here is the temperature at which the DI reached 0.5. Dashed lines are shown in FIG. 5 at the DI level and temperature at which values were measured to correlate to MRV. All those parameters can distinguish the different behavior in this case. The preferred parameter in this case is the DI increase at −5° C. FIG. 5 presents a plot of the DI vs. temperature for the three oils tested as the temperature is ramped down from zero to −8° C. In this case, the DI values were determined by subtracting the measured intensity at 0°

| Step | Start temperature, ° C. | End temperature, ° C. | Rate, ° C./minute | Soak at end temperature, sec |
|---|---|---|---|---|
| A | ambient | 20 | 40 | 1800 |
| B | 20 | 60 | 40 | 10 |
| C | 60 | 20 | 40 | 0 |
| D | 20 | 60 | 40 | 10 |
| B | 60 | −4 | 40 | 3600 |

Time of Initial Intensity Measurement from start of step A
(Sec.): 2170 (about 74 sec after −4° C. is reached in step E)

| Sample | Pour point (D97), ° C. | No flow point (D5985), ° C. | MRV yield stress at −20° C., Pa[1] | MRV visc at −20° C., centipoise[2] | DI (soak at 0° C.) | DI (soak at −4° C.) |
|---|---|---|---|---|---|---|
| 1 | −6 | −6 | <35 | 36228 | 0 | 16.4 |
| 2 | −6 | −6 | >140 | 57400 | 0 | 75.6 |
| 3 | −6 | −7 | <35 | 33400 | 0.1 | 4.7 |

[1]MRV yield stress target for the formulated oil is <35 Pa @ −20° C.
[2]MRV viscosity target at −20° C. for the formulated oils is ≦60,000 cP Thus, for these oils for this formulation under the recited test conditions a DI of about 20 and less at −4° C. best correlates to passing the low temperature MRV property target specifications of 60,000 cP maximum viscosity and <35 Pa maximum yield stress at −20° C.

EXAMPLE 4

Control of MRV in 20W-50 Engine Oil (Formulation 1) Using Primarily 600 SUS Base Stock Using Temperature Ramp The samples in the example above (Example 3) were tested using the same equipment as was used in Examples 1, 2 and 3 and in a temperature ramp as in Embodiment 2 rather than a constant soaking temperature. Before being put in the test cell, the oil samples were heated in vials to a temperature of 100° C. and held there for about 1 hour.

C. from the measured intensities at subsequent lower temperature, that is, the intensity at 0° C. established the zero intensity base line.

Formulated oil low temperature viscometric properties for the three oils are presented below and correlated to the DI increase at −5° C. for each oil.

| Sample | MRV yield stress at −20° C., Pa | MRV visc at −20° C., Centipoise | Onset temperature, ° C. | Temperature to reach 20 DI, ° C. | DI increase at −5° C. |
|---|---|---|---|---|---|
| 1 | <35 | 36200 | −2.7 | −6.2 | 9.2 |
| 2 | >140, <175 | 57400 | −2.0 | −3.5 | 84.2 |
| 3 | <35 | 33400 | −4.6 | −6.6 | 1.7 |

Thus, for these oils for this formulation under the recited test conditions a DI at −5° C. of up to 9.2 but less than 84.2 best correlates with passing the MRV low temperature properties of interest. Comparing Example 3 with Example 4, both of which used the same oil samples, it is seen that for the correlation and DI values to be meaningful, the tests have to be conducted in the same way for each oil sample (the test conditions must be consistent between samples). Thus, data generated using Embodiment 1 cannot be applied against a data base generated using Embodiment 2, and vice versa. Consistency in treating and testing the samples is necessary to ensure that the data obtained can be applied to any given data base, the treating and testing applied to any sample being the same as that used to generate the data base. That is, information in a data base generated using Embodiment 1 will be useful and give meaningful information regarding unknown samples only when and if the unknown samples are treated and tested according to the Embodiment 1 procedures used to generate the data base. The same is true if Embodiment 2 was used to generate the data base, then the unknown samples would have to be treated and tested according to the Embodiment 2 procedure used to generate the data base.

change in response to changes to the formulation in which the low temperature property is measured. The method will provide accurate predictions through adjustments to the correlation to DI that take place in step b10 of Embodiment 1 or step b6 of Embodiment 2.

| Sample | No flow point (D5985), ° C. | MRV yield stress at −20° C., Pa[1] | MRV visc at −20° C., centipoise[2] | Onset temp., ° C. | Temp. to reach 20 DI, ° C. | DI increase at −5° C. |
|---|---|---|---|---|---|---|
| 1 | −6 | <70 | 34400 | −2.7 | −6.2 | 9.2 |
| 3 | −7 | <70; <35 | 3400, 33600 | −4.6 | −6.6 | 1.7 |
| 4 |   | <280 | 68500 | −3.0 | −4.9 | 22.3 |
| 5 | −7 | <35 | 38100 | −5.4 | −8.2 | 0.2 |

[1]MRV yield stress target for the formulated oil is <35 Pa @ −20° C.
[2]MRV viscosity target at −20° C. for the formulated oil is ≦60,000 cP.

EXAMPLE 5

Control of MRV in 20W-50 Engine Oil (Formulation 2) Using Primarily 600 SUS Base Stock Using Temperature Ramp Samples 1 and 3 from Examples 3 and 4 were also tested in a second 20W-50 engine oil using primarily 600 SUS base stock, as were two more samples, 4 and 5, but in this case the formulated oil employed a different pour point depressant than in Formulation 1. Samples were tested using the same equipment as was used in Examples 1, 2, and 3 and with the same temperature ramp as in Example 4. The samples were also heated in vials to a temperature of 100° C. and held there for about 1 hour before being put in the test cell, as in Example 4.

In this example, sample 1, when blended into the 20W50 engine oil, is a marginal fail in the MRV test because its yield stress was >35 Pa but <70 Pa, while the requirement is <35 Pa. Sample 3 passes this requirement. Sample 4 is a poor fail in this test because its yield stress was <280, but >245 Pa and it also failed the viscosity requirement of ≦60,000 cP. Sample 5 is borderline, passing in one test and failing in a repeat test.

Figure 6:
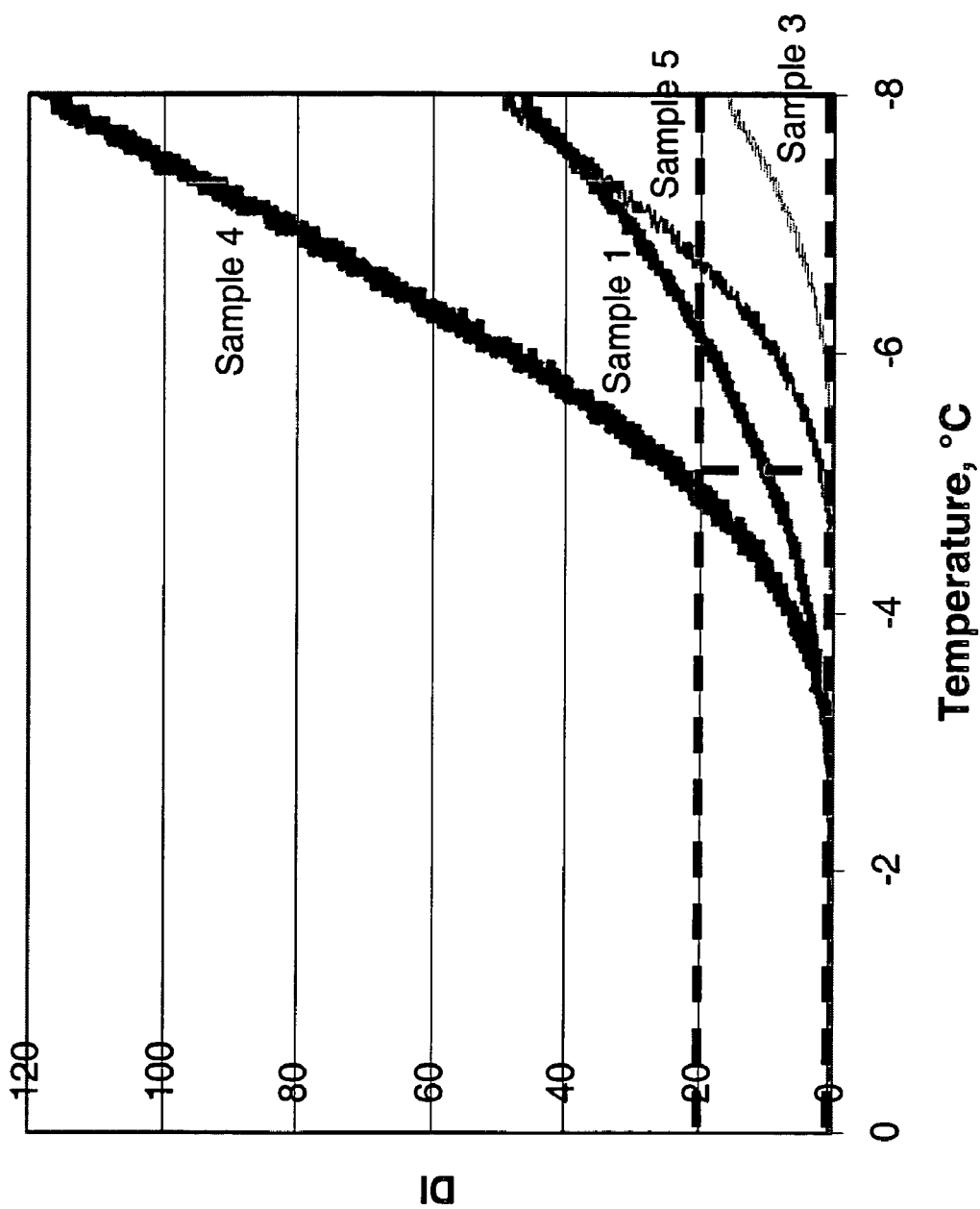
FIG. 6 presents a plot of DI versus temperature for four 600 SUS basestock oils tested to formulate a 20W50 engine oil (Formulation 2) showing the DI for each sample as the temperature was ramped down from zero to −8° C.

In this example, the onset temperatures do not correlate well with MRV, because the poorly failing sample 4 has a lower onset temperature than the marginally failing sample 1. See FIG. 6. For these oils for this formulation under the recited test conditions, a DI at −5° C. of up to 0.2 but less than about 1.7 correlates with passing the MRV low temperature property of interest. Comparing this example to Example 4 makes is clear that the DI limit values correlating with the pass/fail of the formulated oil in respect to the selected low temperature viscometric property of interest may need to

EXAMPLE 6

Control of MRV in Engine Oils (5W-30) Formulated with Group II Light Neutral Base Stocks It is required for product certification that the MRV viscosity and yield stress of engine oils be less than specified values. One such formulation contains 82 wt % of a 120 SUS Group II base stock. The target pour point for these base stocks is −18° C. The formulated oils were blended with the same performance additive components, except that different 120 SUS base stocks were used. The basestocks have the same cloud point and pour point, the tests commonly used to ensure good performance, and therefore would have been expected to perform in the same manner in low temperature testing. However, the MRV behavior of lubricants blending with these two base stocks is much different.

The same equipment was used as in the previous examples.

The table below shows the good correlation of DI using a temperature ramp, Embodiment 2, to the MRV. Prior to introduction into the test cell, the oil samples were heated to 100° C. in vials and held at that temperature for about 1 hour.

| Step | Start temperature, ° C. | End temperature, ° C. | Rate, ° C./minute | Soak at end temp., second |
|---|---|---|---|---|
| A | ambient | 20 | 40 | 1800 |
| B | 20 | 60 | 40 | 10 |
| C | 60 | 20 | 40 | 0 |
| D | 20 | 60 | 40 | 10 |
| E | 60 | −8 | 40 | 10 |
| F | −8 | −22 | 0.25 |   |

Figure 7:
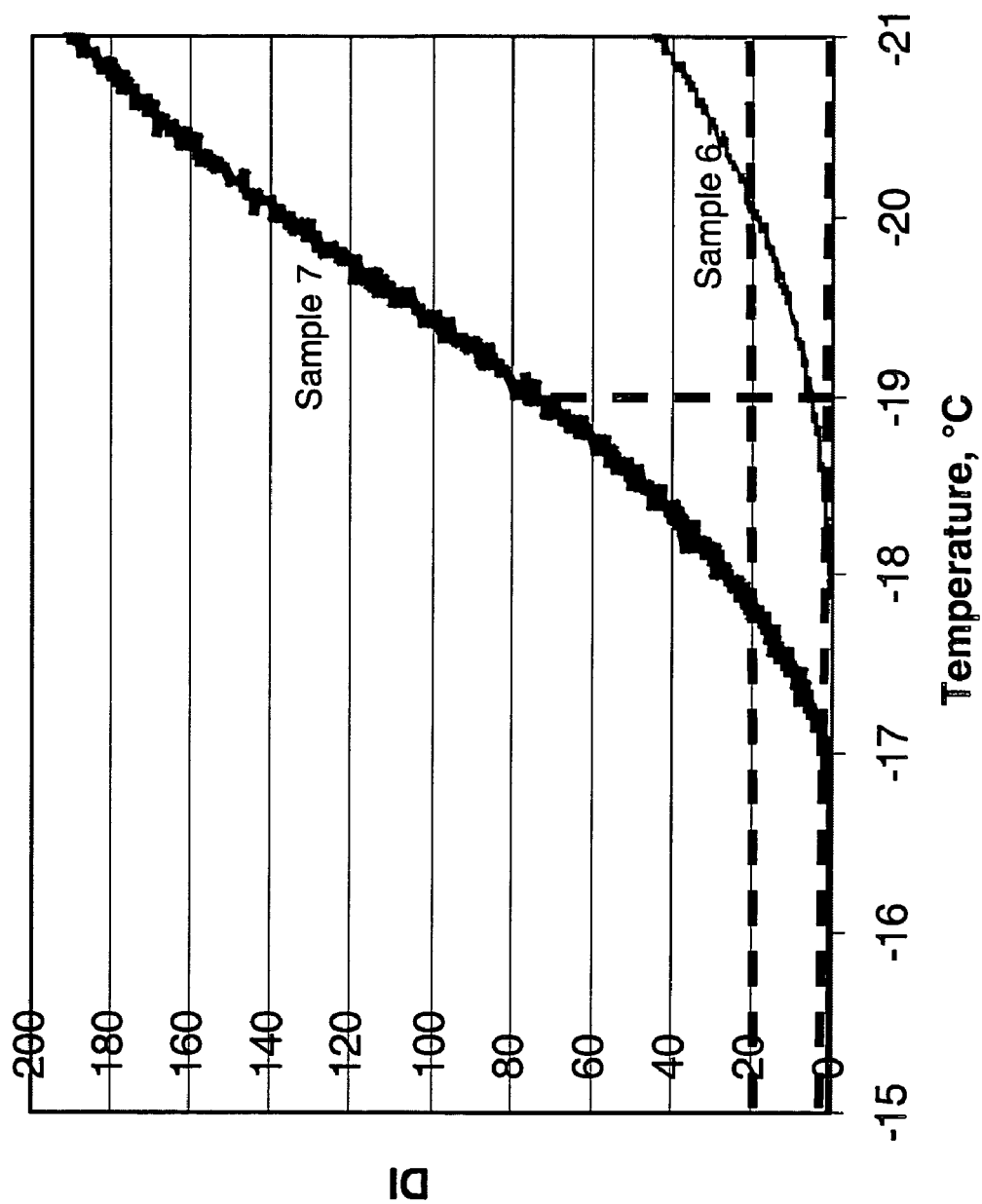
FIG. 7 presents a plot of DI versus temperature for two Group II light neutral base stocks tested to formulate as engine oil showing the DI for each sample as the temperature was ramped down from −15° C. to −21° C.

Various parameters are available to control the MRV, including an onset threshold, temperature to reach a given signal increase, and signal increase at a given temperature. All those parameters can distinguish the different behavior in this case. The preferred parameter in this case is the DI increase at −19° C. FIG. 7 presents a correlation between the change in signal intensity (DI) versus temperature as the temperature is ramped down from −14° C. to −22° C. for two Group II Light neutral base oils, the figure showing the changes between −15° C. to −21° C.

| Sample | Pour point (D5950), ° C. | Cloud point (D2500), ° C. | MRV yield stress at −35° C., Pa[(1)] | MRV visc at −35° C., centipoise[(2)] | Onset temp, ° C. | Temp. to reach 20 DI, ° C. | DI increase at −19° C. |
|---|---|---|---|---|---|---|---|
| 6 | −18 | −13 | <35 | 18600 | −17.9 | −20.0 | 5.7 |
| 7 | −18 | −13 | <35 | 98500 | −16.8 | −17.9 | 74.4 |

[(1)]MRV yield stress target for the formulated oil is <35 Pa @ −35° C.
[(2)]MRV yield stress target at −35° C. for the formulated oil is ≦60,000 cP.

EXAMPLE 7

Control of Brookfield Viscosity in Hydraulic Oils

It is desirable that the Brookfield viscosity of a hydraulic oil used in some applications be kept to a minimum for optimal performance. The oil contains 59 wt % of a 100 SUS base stock. The target pour point for these base stocks is −18° C. The hydraulic oils were blended with the same performance components, except that a variable amount of wax was added to simulate undesirable leakage of wax into a base stock during manufacturing at a refinery. All components were blended at 100° C. for 1-2 hours to ensure complete dissolution of the wax. The same equipment was used as in the previous examples. The table below shows the good correlation of DI to Brookfield viscosity when a constant temperature of −4° C. is used in the final soaking step of the DI measurement employing Embodiment 1 using the same temperature program as recited in Example 3.

| % wax | DI (soak at −4° C.) | Brookfield viscosity at −30° C., centipoise |
|---|---|---|
| 0 | 0 | 2320 |
| 0.3 | 0 | 2380 |
| 0.6 | 4.8 | 2460 |
| 1.0 | 45.0 | 2760 |

The Brookfield vis target at −30° C. for the oil product is 2800 cP maximum. Therefore DI values of about 45 indicate that the performance will be marginal but at values of less than 45, and preferably about 5 DI and less the performance will be good.

EXAMPLE 8

Control of Brookfield Viscosity in Automatic Transmission Oils

It is desirable that the Brookfield viscosity of an automatic transmission oil be kept to a minimum for optimal performance. The ATF oil studied contains 57 wt % of a 100 SUS base stock. The target pour point for 100 SUS base stocks is −18° C. The oil was blended with the same performance additive components, except that a variable amount of wax was deliberately added to simulate undesirable leakage of wax into a base stock during manufacturing at a refinery. All components were blended at 100° C. for 1-2 hours to ensure complete dissolution of the wax. The same equipment was used as in the previous examples. The table below shows the good correlation of DI to Brookfield viscosity when a constant temperature of −4° C. is used in the final soaking step of the DI measurement employing Embodiment 1 (same temperature program as in example 3).

| % wax | DI (soak at −4° C.) | Brookfield viscosity at −40° C., centipoise |
|---|---|---|
| 0 | 0 | 13320 |
| 0.1 | 0 | 13360 |
| 0.3 | 0 | 13560 |
| 0.6 | 4.8 | 13920 |
| 1 | 45.0 | 19700 |

The Brookfield viscosity target at −40° C. for this oil product is 20,000 cP maximum. Thus, DI values of about 45 indicate that the performance of a product formulated from the oil sample will be marginal but at DI values below 45 and preferably about 5 DI and less at −4° C. as evidenced for the other samples performance will be good.

It is merely a coincidence that the level of DI values that correlate to passing performance in the hydraulic oil of Example 7 and the ATF of Example 8 are the same. In general, the additives and co-basestocks and the type, temperature and other conditions of the low temperature test will all influence and be reflected in difference in the exact level of DI and the temperature at which it is measured that ensures passing a viscometric property parameter target for different types of formulated oil products.

What is claimed is:

1. A method for determining, in real time, the suitability of basestock oils for use as the basestocks in the production of fully formulated lubricating oils meeting product low temperature viscometric properties, which method comprises:
 (a) selecting at least one low temperature viscometric property of the fully formulated lubricating oil selected from mini-rotary viscometer (MRV) viscosity, yield stress, Brookfield viscosity, cold cranking simulator (CCS) and pour point,
 (b) producing a training set by:
  (1) securing a sample of dewaxed basestock oil;
  (2) heating the basestock oil sample for a time and to a temperature sufficient to melt all the wax in the sample;
  (3) agitating the heated sample to insure homogeneity;
  (4) cooling the oil in a sample cell equipped with heating and cooling means and instrumented for the measurement of reflection of light or transmittance of light generated by a source, said cooling being to a selected target temperature in the range of between about 20° C. above the base oil specification pour point and about 5° C. below the base oil specification pour point;
  (4a) waiting for the sample and test cell to stabilize;
  (5) measuring the signal of scattered/reflected light off of or transmitted light through the sample at the temperature of step 4 after the stabilization period to secure a first intensity reading;

(6) holding the sample at the target temperature of step 4 for from 1 minutes to 3 hours;

(7) measuring the signal of scattered/reflected or transmitted light at the end of the hold time of step 6 to secure a second intensity reading and measuring any change in signal intensity (delta intensity of signal) between the first signal and the second signal reading;

(8) formulating an oil product using the basestock and measuring the selected low temperature viscometric property or properties of step (a) associated with product quality;

(9) repeating steps 1-8 with one or more additional samples of the same or different dewaxed base stock oils using different target temperatures between 20° C. above and 5° C. below the specification pour point, as needed, until a relationship is observed between the delta intensity of signal and the selected low temperature formulated oil viscometric property or properties of choice;

(10) correlating the delta intensity of signal to the selected low temperature viscometric property or properties;

(c) subjecting a base oil to steps 1-8;

(d) comparing the delta intensity of signal of the base oil of step (c) with the correlation data base to predict whether a formulated lubricating oil possessing the selected low temperature viscometric property or properties can be made using said base oil.

2. A method for determining, in real time, the suitability of base stock oils for use as the base stocks in the production of fully formulated lubricating oil products meeting product low temperature viscometric properties, said method comprising:

(a) selecting at least one low temperature viscometric property of the fully formulated lubricating oil selected from mini-rotary viscometer (MRV) viscosity, yield stress, Brookfield viscosity, cold cranking simulator (CCS) and pour point;

(b) producing a training set by:

(1) securing a sample of dewaxed basestock oil to be used in producing the fully formulated oil;

(2) heating the basestock for a time and to a temperature sufficient to melt all the wax in the sample;

(3) agitating the sample to insure homogeneity;

(4) slowly cooling the sample in a sample cell equipped with heating and cooling means and fitted for the measurement of reflection of light or transmittance of light generated by a source, said cooling being to a target temperature from about 20° C. above to about 5° C. below the pour point specification of the oil, measuring the reflection/scattering or transmittance signal, and measuring the ongoing change in signal intensity (delta intensity of signal) during said cooling;

(5) formulating an oil produced using the basestock oil and measure the selected low temperature viscometric property or properties of step (a) associated with product quality;

(6) correlating the delta intensity of signal to the selected low temperature viscometric property or properties;

(c) subjecting a base oil to steps 1-4 with one or more additional samples of the same or different dewaxed base stock oils;

(d) comparing the delta intensity of signal for the base oil of step (c) with the correlation data base to predict whether a formulated lubricating oil possessing the selected low temperature viscometric property or properties can be made using said base oil.

3. The method of claim 1 or 2 wherein the heating of step (b)(2) is for a time and to a temperature sufficient to melt all the wax in the sample and to remove any water present in the sample.

4. The method of claim 1 or 2 wherein a cooling step 3(a) is practiced whereby the sample is cooled to ambient conditions and the rate of cooling to ambient condition is between about 5° C/min. to 100° C/min.

5. The method of claim 1 wherein the rate of cooling the sample to the temperature between about 20° C. above to about 5° C. below the base oil specification pour point is in the range of between about 20° C/min. to 60° C/min.

6. The method of claim 1 wherein the period of stabilization of step (4a) ranges from zero to 600 seconds.

7. The method of claim 1 wherein the holding period of step (b)(6) ranges from about 30 minutes to about 90 minutes.

8. The method of claim 1 or 2 wherein the reflected or transmitted light is in the ultraviolet, visible or infrared wavelength region of the spectrum.

9. The method of claim 1 wherein one or more additional samples of the same or of different dewaxed base stock oils are subjected individually to steps (b)(1-9) to create a data base of delta intensity of signal versus the selected formulated lubricating oil low temperature viscometric property or properties for a multiplicity of base oil samples.

10. The method of claim 2 wherein one or more additional samples of the same or of different dewaxed basestock oils are subjected individually to steps (b)(1-5) to create a data base of delta intensity of signal versus the selected formulated lubricating oil low temperature viscometric property or properties for a multiplicity of base oil samples.

11. The method of claim 2 wherein the cooling of the sample over the temperature range of about 20° C. above to about 5° C. below the specification pour point of the base oil is at a rate of about 0.1° C. to 1° C/min.

12. The method of claim 2 wherein the selected low temperature viscometric property or properties are correlated to the temperature at which the intensity of signal begins to increase (onset temperature).

13. The method of claim 2 wherein the selected low temperature viscometric property or properties are correlated to the temperature at which a given delta intensity of signal is reached.

14. The method of claim 2 wherein the selected low temperature viscometric property or properties are correlated to any combination of temperatures at which given delta intensities of signal are reached and delta intensities at given temperatures.

\* \* \* \* \*